US007921737B2

(12) United States Patent
Sparks et al.

(10) Patent No.: US 7,921,737 B2
(45) Date of Patent: Apr. 12, 2011

(54) MICROFLUIDIC DEVICE AND METHOD OF OPERATION

(75) Inventors: Douglas Ray Sparks, Whitmore Lake, MI (US); Richard Thayre Smith, Saline, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 112 days.

(21) Appl. No.: 12/369,118

(22) Filed: Feb. 11, 2009

(65) Prior Publication Data
US 2010/0037708 A1 Feb. 18, 2010

Related U.S. Application Data

(60) Provisional application No. 61/065,293, filed on Feb. 11, 2008.

(51) Int. Cl.
*G01F 1/84* (2006.01)
(52) U.S. Cl. .................................................. 73/861.355
(58) Field of Classification Search .................. None
See application file for complete search history.

(56) References Cited

U.S. PATENT DOCUMENTS

| 6,336,369 | B1 * | 1/2002 | Gomi et al. ............... 73/861.357 |
| 6,363,794 | B1 * | 4/2002 | Van Cleve ................ 73/861.357 |
| 6,477,901 | B1 * | 11/2002 | Tadigadapa et al. ...... 73/861.352 |
| 6,516,674 | B1 * | 2/2003 | Poremba ................... 73/861.357 |
| 6,935,010 | B2 * | 8/2005 | Tadigadapa et al. ......... 29/592.1 |
| 7,228,735 | B2 * | 6/2007 | Sparks et al. .............. 73/204.26 |
| 7,263,882 | B2 * | 9/2007 | Sparks et al. .............. 73/204.26 |
| 7,287,438 | B2 * | 10/2007 | Van Cleve ................ 73/861.355 |
| 7,437,912 | B2 * | 10/2008 | Sparks et al. ................. 73/54.01 |
| 7,597,007 | B2 * | 10/2009 | Van Cleve et al. ....... 73/861.355 |
| 2009/0075129 | A1 * | 3/2009 | Sparks et al. ................... 429/13 |

FOREIGN PATENT DOCUMENTS
EP 1207375 A1 * 5/2002

OTHER PUBLICATIONS

D. Sparks, R. Smith, S. Massoud-Ansari, N. Najafi; Coriolis Mass Flow, Density and Temperature Sensing with a Single Vacuum Sealed MEMS Chip; Solid State Sensor, Actuator and Microsystems Workshop, Jun. 6-10, 2004, pp. 75-78.
D. Sparks, R. Smith, R. Schneider, J. Cripe, S. Massoud-Ansari, A. Chimbayo, N. Najafi; A Variable temperature, resonant density sensor made using an improved chip-level vacuum package; Sensors and Actuators A107, 2003, pp. 119-124.
D. Sparks, V. Cruz, N. Najafi; The resonant behavior of silicon tubes under two-phase microfluidic conditions with both microbeads and gas bubbles; Sensors and Actuators A 135, Sep. 2006, pp. 827-832.

* cited by examiner

*Primary Examiner* — Harshad Patel
(74) *Attorney, Agent, or Firm* — Hartman & Hartman, P.C.; Gary M. Hartman; Domenica N. S. Hartman

(57) ABSTRACT

A microelectromechanical system (MEMS) device and method for operating the device to determine a property of a fluid. The device has a tube that extends from a base and is spaced apart from a substrate surface for vibrational movement in a plane normal to the surface. The tube defines a continuous internal passage having a fluid inlet and fluid outlet fluidically connected to the base. A cantilevered member attached to a distal portion of the tube opposite the base is configured for vibrational movement relative to the distal portion. A drive electrode operable to induce vibrational movements in the tube and cantilevered member is disposed on the substrate surface. Sensing electrodes are disposed on the substrate surface for sensing Coriolis-induced deflections of the tube when vibrated, generating outputs from which a property of a fluid flowing through the tube can be determined.

24 Claims, 4 Drawing Sheets

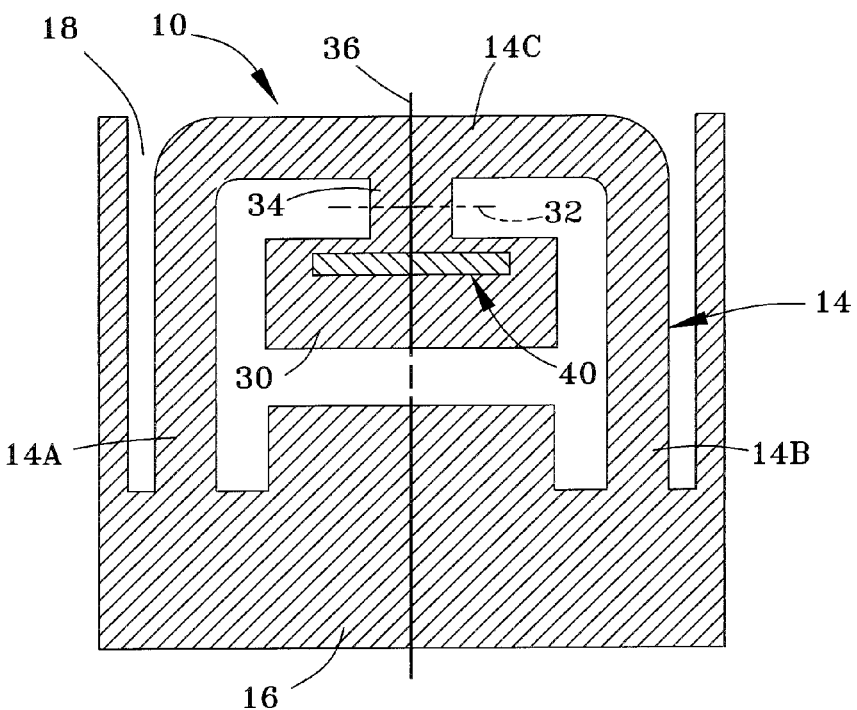
FIG.3
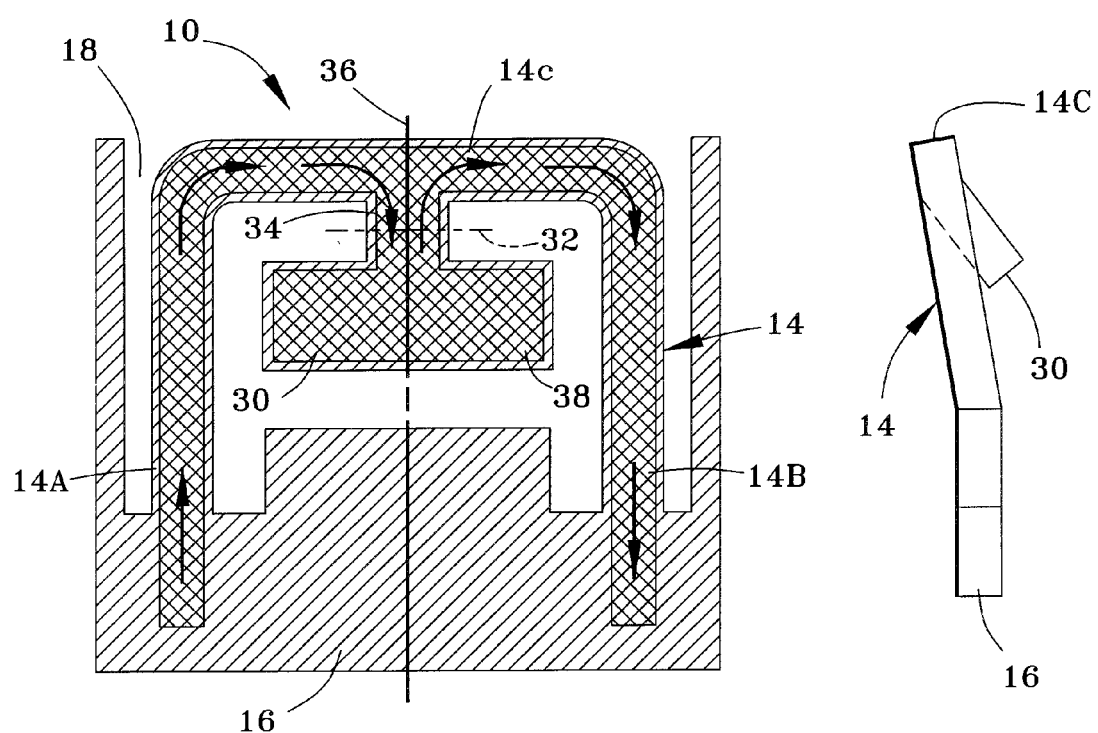
FIG.4
FIG.5

MICROFLUIDIC DEVICE AND METHOD OF OPERATION

CROSS REFERENCE TO RELATED APPLICATIONS

This application claims the benefit of U.S. Provisional Application No. 61/065,293 filed Feb. 11, 2008, the contents of which are incorporated herein by reference.

BACKGROUND OF THE INVENTION

The present invention generally relates to devices and methods for measuring properties of fluids. More particularly, this invention relates to a microfluidic device equipped with a resonating structure, a microchannel within the resonating structure through which a fluid flows, and means for ascertaining properties of the fluid while flowing through the microchannel. The performance of the device is improved with the addition of means capable of minimizing mechanical losses resulting from the mechanical energy of the resonating structure being dissipated to a supporting substrate.

Fluid delivery devices capable of precise measurements find use in a variety of industries, nonlimiting examples of which include medical treatment systems such as drug infusion and anesthesia, energy and fuel systems including fuel delivery systems and fuel cells such as direct methanol fuel cells (DMFC), and consumer goods. Various types of flow rate and concentration sensors have been proposed, including electrolytic, refractometer, ultrasonic, electrochemical, electromagnetic, and electromechanical sensors. An example of the latter is a Coriolis-based microfluidic device disclosed in commonly-assigned U.S. Pat. No. 6,477,901 to Tadigadapa et al., whose contents relating to the fabrication and operation of a Coriolis-based sensor are incorporated herein by reference.

Coriolis-based microfluidic devices of the type disclosed by Tadigadapa et al. include a micromachined tube supported above a substrate to have a freestanding portion. Drive and sensing electrodes are located on the substrate surface beneath the freestanding portion of the tube. The drive electrode can be, for example, capacitively coupled to the freestanding portion of the tube for capacitively (electrostatically) driving the freestanding portion at or near resonance, while the sensing electrodes sense (e.g., capacitively, optically, etc.) the deflection of the resonating tube relative to the substrate and provide feedback to enable the vibration frequency induced by the drive electrode to be controlled with appropriate circuitry. In use, while a fluid flows through an internal passage within the tube, the freestanding portion is vibrated at or near resonance by the drive electrode to ascertain certain properties of the fluid, such as flow rate and density, using Coriolis force principles. In particular, as the freestanding portion is driven at or near resonance by the drive electrode, the sensing electrodes sense a twisting motion of the freestanding portion, referred to as the Coriolis effect, about the axis of symmetry of the freestanding portion. The degree to which the freestanding portion twists (deflects) during a vibration cycle as a result of the Coriolis effect can be correlated to the mass flow rate of the fluid flowing through the tube, while the density of the fluid is proportional to the frequency of vibration at resonance.

Notable advantages of Coriolis-based microfluidic devices include the miniaturized scale to which they can be fabricated using semiconductor technology. As taught by Tadigadapa et al., the structural components of the device can be combined with electronics on a single chip by micromachining techniques, such as bulk etching and surface thin-film etching, to yield a microelectromechanical system (MEMS) capable of precisely analyzing very small quantities of fluids. When suitable miniaturized, a Coriolis-based microfluidic device can be enclosed by a capping wafer to allow for vacuum packaging that further improves the performance of the device by reducing air damping effects.

The microfluidic device disclosed in Tadigadapa et al. can be used in a wide variety of applications, as evident from commonly-assigned U.S. Pat. Nos. 6,637,257, 6,647,778, 6,932,114, 7,059,176, 7,228,735, 7,263,882, 7,354,429 and 7,437,912, U.S. Published Patent Application Nos. 2004/0171983, 2005/0126304, 2005/0284815, 2005/0235759, 2006/0211981, 2007/0151335, 2007/0157739, 2008/0154535, and pending U.S. patent application Ser. Nos. 12/031,839, 12/031,860, 12/106,642 and 12/143,942. As particular examples, U.S. Pat. No. 7,263,882 teaches that chemical concentrations, including those of fuel cell solutions, can be measured by sensing changes in fluid density as a fluid sample flows through a microchannel within a resonating tube of a MEMS-based Coriolis microfluidic device, and U.S. Published Patent Application No. 2007/0157739 teaches the capability of detecting potential measurement errors attributable to second phases such as gas bubbles in a fluid being evaluated by a resonating tube of a MEMS-based Coriolis microfluidic device.

While exhibiting very high sensitivity to mass flow rate, density and various other properties of a fluid, the performance of MEMS-based Coriolis microfluidic devices of the type taught by Tadigadapa et al. is subject to mechanical losses resulting from the attachment of the resonating tube to a substrate. In particular, clamping losses occur as a result of the tube's substrate anchor (attachment) to the MEMS substrate being stressed by tube displacement. A fraction of the vibration energy is lost from the tube though wave propagation into the MEMS substrate. While accounting for only a fraction of the vibration energy, clamping losses are sufficient that optimum performance requires a relatively large packaging mass to dissipate the mechanical energy loss and isolate the resonating tube from external mechanical stress and vibration. As such, further improvements in the sensitivities of MEMS-based Coriolis microfluidic devices are desired to fully realize the capabilities of these devices.

BRIEF SUMMARY OF THE INVENTION

The present invention provides a microelectromechanical system (MEMS) device and a method for operating the device to determine at least one property of a fluid. The invention provides the capability of improving the performance of the device by minimizing clamping losses attributable to the attachment of a resonating tube to a substrate.

According to a first aspect of the invention, the MEMS device comprises a structure on a substrate. The structure comprises a base and a tube extending from the base and spaced apart from a surface of the substrate so as to be capable of vibrational movement in a plane normal to the surface of the substrate. The tube comprises a continuous internal passage, a fluid inlet and a fluid outlet of the internal passage fluidically connected to the base, and a distal portion relative to the base. A cantilevered member is attached to the distal portion of the tube and configured for vibrational movement relative to the distal portion and in a plane normal to the surface of the substrate. At least one drive electrode is disposed on the surface of the substrate adjacent the cantilevered member and/or the distal portion of the tube, and is operable to induce the vibrational movements of the tube and the cantilevered member. Sensing electrodes are disposed on the surface of the substrate and adapted to sense deflections of the tube when vibrated with the drive electrode and produce outputs corresponding to the sensed deflections. Finally, means is provided for determining from the outputs at least one property of the fluid flowing through the internal passage.

According to a second aspect of the invention, the method entails operating the MEMS device to sense at least one property of the fluid. The method comprises operating the at least one drive electrode to induce the vibrational movements of the tube and the cantilevered member as the fluid flows through the internal passage within the tube so that the vibrational motion of the cantilevered member is not in phase with the vibrational motion of the tube. The sensing electrodes are operated to sensing the deflections of the tube relative to the substrate, and outputs are produced that correspond to the sensed deflections and from which the at least one property of the fluid is determined.

According to a preferred aspect of the invention, the location of the cantilevered member is preferably chosen to enhance the performance of the MEMS device. More particularly, the cantilevered member is preferably configured and used as a counterbalance to the mass of the tube and the fluid within the tube, and the vibrational movement of the cantilevered member is preferably about 180 degrees out of phase with the vibrational movement of the tube, thereby minimizing the mechanical (clamping) losses that are dissipated to the substrate. This aspect of the invention can be utilized to promote the sensitivity of the MEMS device, and/or allow for the use of packaging processes and materials that are less expensive that conventional MEMS devices. In addition, the presence and operation of the cantilevered member can potentially allow mechanical stresses applied to the package from adversely impacting the performance of the device.

Other objects and advantages of this invention will be better appreciated from the following detailed description.

BRIEF DESCRIPTION OF THE DRAWINGS

FIG. 3 is a plan view of the micromachine level of a microfluidic device similar to the device of FIGS. 1 and 2, but with the tube having a different shape in accordance with a third embodiment of this invention.

FIG. 4 is a plan view of the micromachine level of a microfluidic device similar to the device of FIG. 3, but with the cantilevered member having an internal chamber fluidically coupled to the tube in accordance with a fourth embodiment of this invention.

FIG. 5 is a side view showing the tube and cantilevered member of the devices of FIGS. 1 through 4 vibrating out of phase with each other.

DETAILED DESCRIPTION OF THE INVENTION

Figure 1:
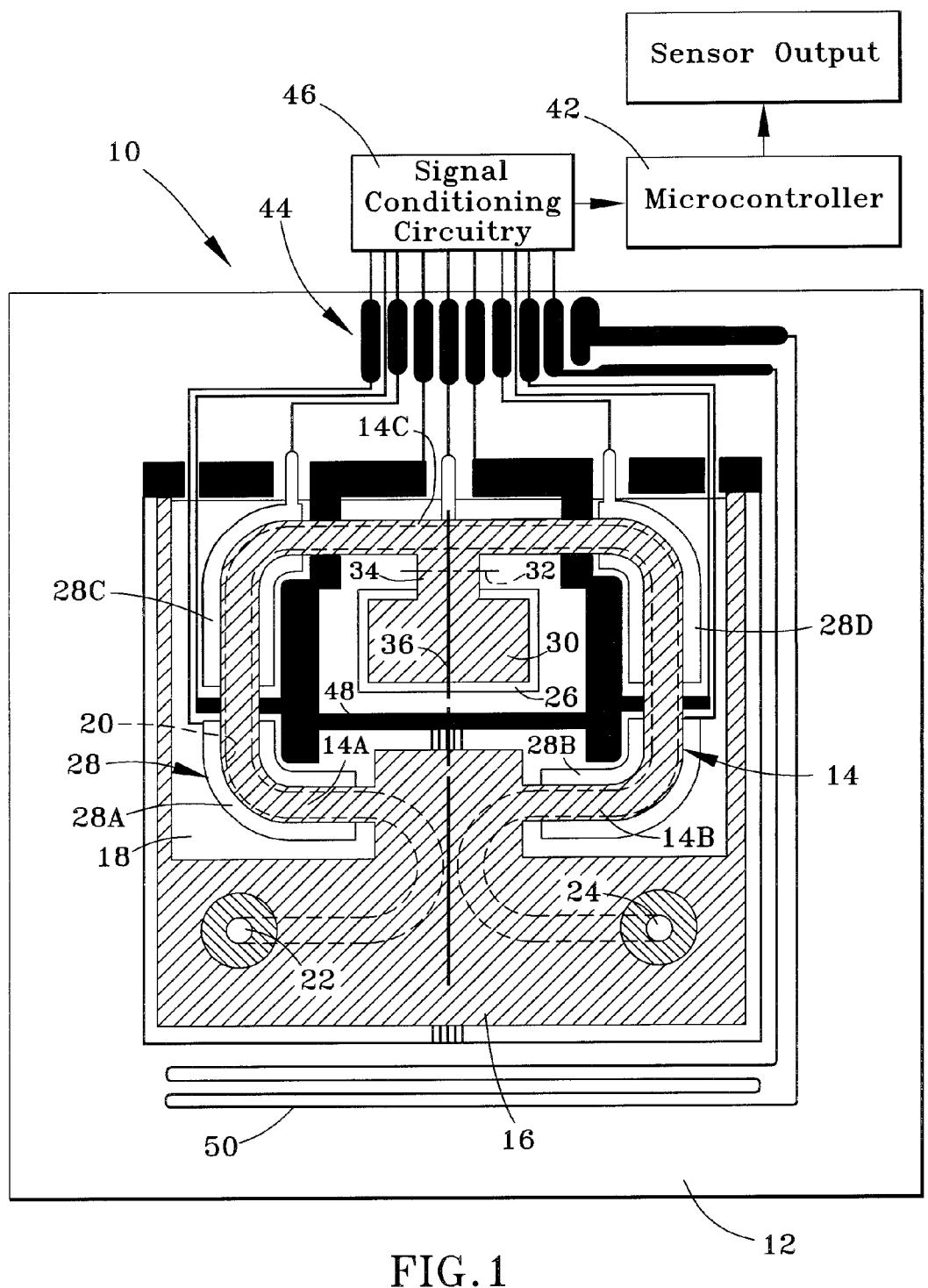
FIG. 1 is a plan view of a microfluidic device with a resonating micromachined tube, a cantilevered member, and a drive electrode beneath the cantilevered member in accordance with a first embodiment of this invention.

FIGS. 1 through 7 represent MEMS microfluidic devices 10 similar in construction and operation to the MEMS microfluidic device disclosed by Tadigadapa et al., but modified to exhibit improved operating characteristics. While the invention will be discussed in reference to the microfluidic devices 10, aspects of the invention are also applicable to other MEMS devices, including motion sensors and RF-MEMS.

In FIGS. 1 through 7, consistent reference numbers are used to identify functionally equivalent structures. Each device 10 is represented as being fabricated on a substrate 12, which can be formed of silicon, doped silicon and other semiconductor materials, quartz, glass materials, ceramic materials, metallic materials including titanium, stainless steels and KOVAR® (a nickel-cobalt ferrous alloy commercially available from Carpenter Technology Corporation), composite materials, and other materials capable of being micromachined. A tube 14 is cantilevered from a base 16 bonded to the substrate 12, such that the tube 14 is suspended above a surface 18 of the substrate 12. The substrate surface 18 beneath the tube 14 is shown as defined by a single recess in the substrate 12 underlying the entire tube 14, though the surface 18 may be defined in any suitable manner to define a gap between the tube 14 and substrate 12. The tube 14 defines a continuous internal passage 20 through which a fluid can flow. In the embodiments shown in the Figures, fluid enters and exits the tube 14 via an inlet 22 and outlet 24 located in the base 16. According to Tadigadapa et al., the tube 14 can be vibrated at or near resonance to determine the mass flow rate and density of the fluid flowing through the tube 14 using Coriolis force principles. The shape and size of the tube 14 can be chosen to provide an adequate flow capacity for the fluid and to have suitable vibration parameters for the intended fluids to be evaluated with the device 10.

Figure 2:
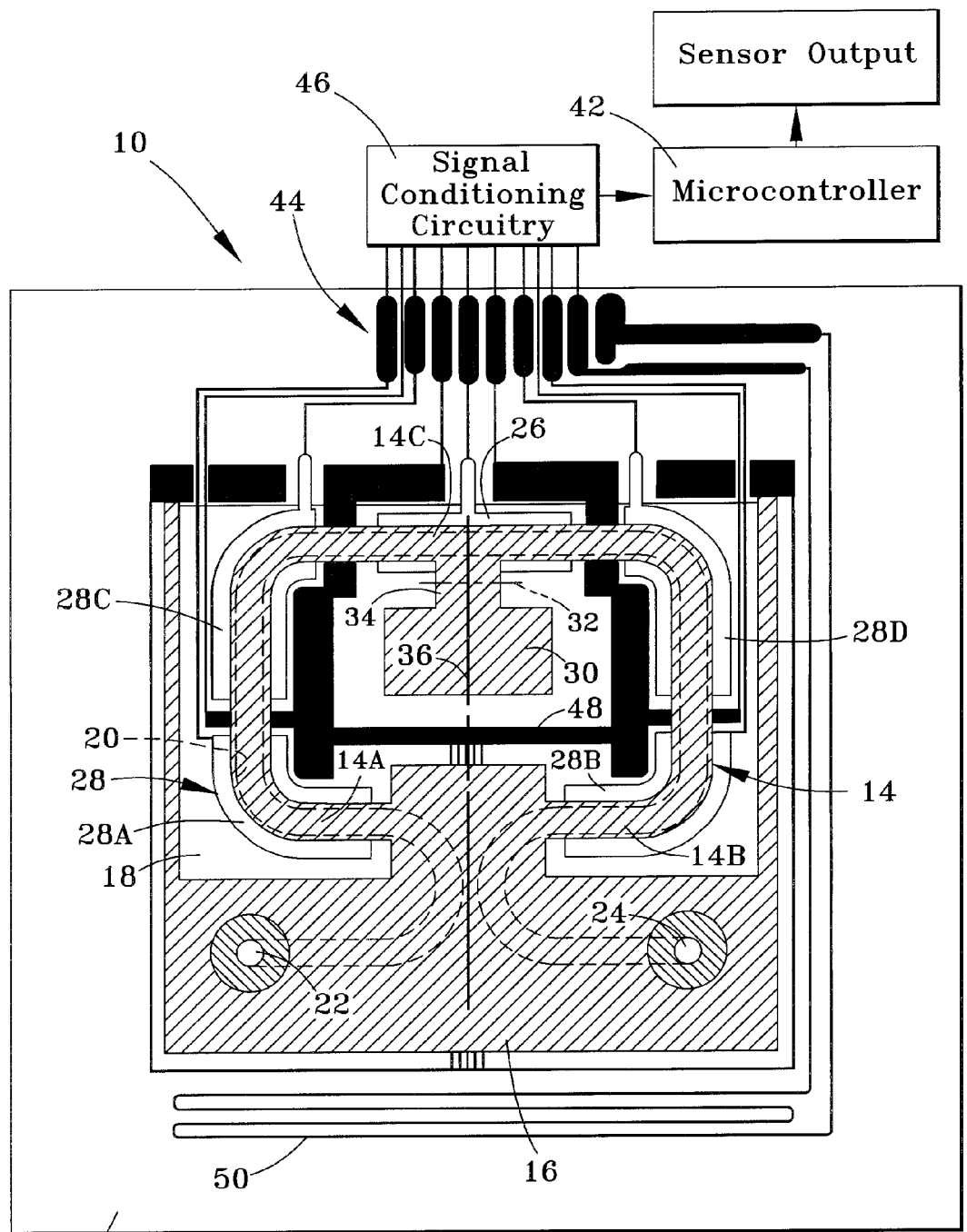
FIG. 2 is a plan view of a microfluidic device similar to the device of FIG. 1, but with the drive electrode beneath the tube in accordance with a second embodiment of this invention.
Figure 6:
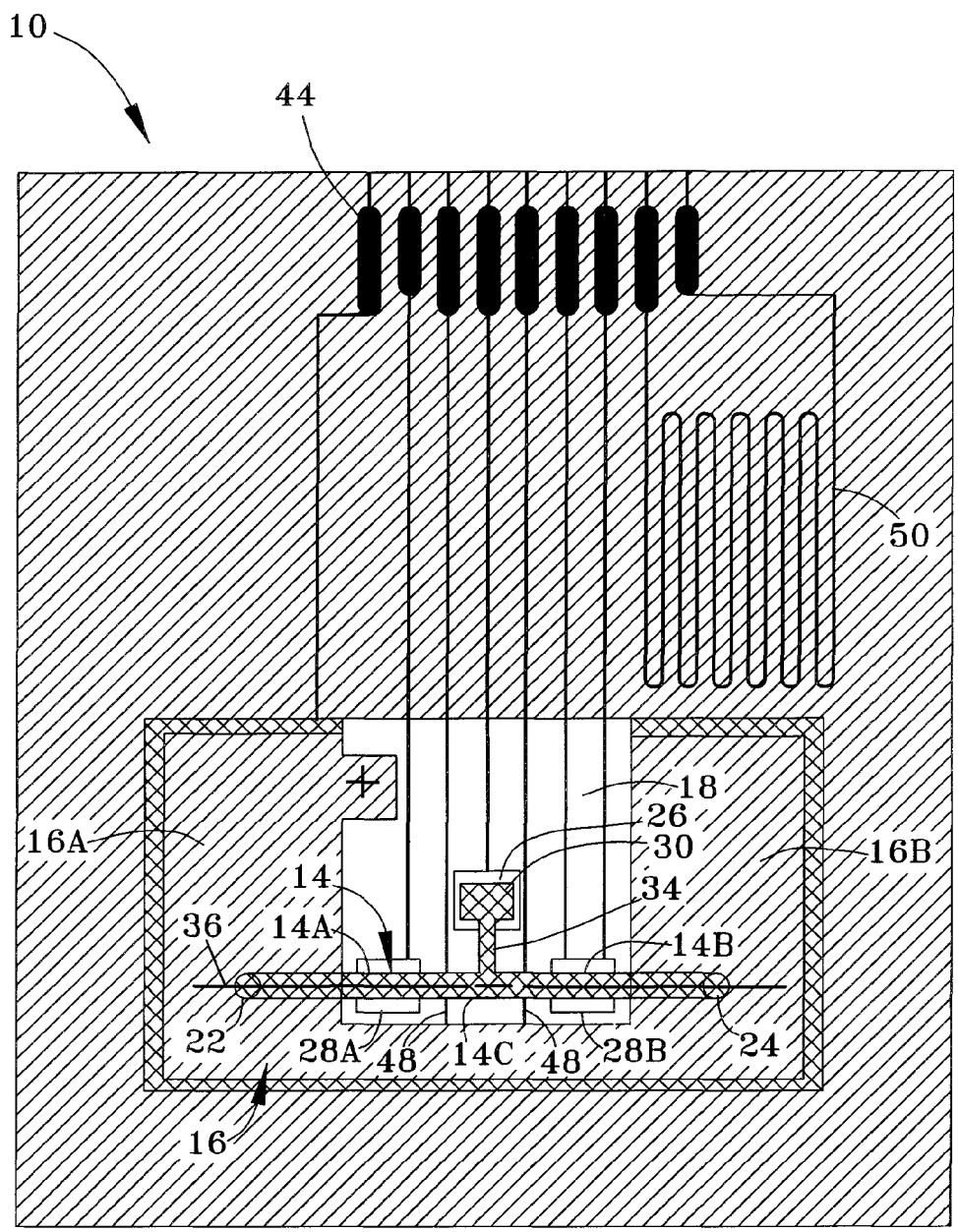
FIG. 6 is a plan view of a microfluidic device similar to the devices of FIGS. 1 through 5, but with the tube having a linear shape in accordance with a fifth embodiment of this invention.

The tube 14 may have a variety of shapes, including but not limited to a generally C-shaped configuration as shown in FIGS. 1 and 2, a generally U-shaped configuration as shown in FIGS. 3 and 4, or a linear or straight shape as shown in FIG. 6. In each case, the tube 14 has proximal portions 14A and 14B attached to the base 16 and a distal portion 14C from the base 16 and midway between the proximal portions 14A and 14B. In FIGS. 1 and 2, the tube 14 is cantilevered from the base 16, the base 16 is between the proximal portions 14A and 14B of the tube 14, the proximal portions 14A and 14B are coaxial, and the distal portion 14C is parallel to the proximal portions 14A and 14B. In FIGS. 3 and 4, the tube 14 is again cantilevered from the base 16, but the proximal portions 14A and 14B of the tube 14 extend in parallel from the base 16 and the distal portion 14C is perpendicular to the proximal portions 14A and 14B. In FIG. 6, the tube 14 is not cantilevered but instead is located between spaced-apart portions 16A and 16B of the base 16, and the proximal and distal portions 14A, 14B and 14C of the tube 14 are coaxial as a result of the linear shape of the tube 14. Other tube shapes—both simpler and more complex—are also within the scope of the invention.

The tube 14, base 16 and internal passage 20 are preferably formed by micromachining, which is known and used herein to refer to techniques for forming very small elements by bulk etching a substrate (e.g., a silicon wafer) or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. The tube 14 and base 16 can either be fabricated entirely from layers of the chosen materials deposited on the substrate 12, or fabricated in part by etching the substrate 12. Because micromachining technologies are employed to fabricate the tube 14, the size of the tube 14 can be extremely small, such as lengths of about 0.5 mm and cross-sectional areas of about 250 µm², with smaller and larger tubes also being within the scope of this invention. Particularly suitable configurations and processes for fabricating resonant mass flow and density sensors using micromachining techniques are disclosed in commonly-assigned U.S. Pat. No. 6,477,901 to Tadigadapa et al., commonly-assigned U.S. Pat. No. 6,647,778 to Sparks, and commonly assigned U.S. Pat. No. 7,381,628 to Sparks et al., whose disclosures relating to micromachining processes are incorporated herein by reference. Because of their miniature size, the micromachined tubes 14 shown in FIGS. 1 through 7 can be used to very accurately determine the mass flow rate, density, and/or specific gravity of a fluid flowing through the tube 14. As such, the devices 10 are suitable for use in a wide variety of applications where accuracy and precision are important, such as chemical concentration applications including but not limited to drug infusion systems, fuel cell systems, and drug and chemical mixing systems. Coriolis force principles can also be used to ascertain the volumetric flow rate, viscosity, lubricity, and other properties of a fluid flowing through the tube 14.

As in Tadigadapa et al., the tube 14 is vibrated in a direction perpendicular to the surface 18 of the substrate 12, preferably at or near its resonant frequency. During half of the vibration cycle in which the tube 14 travels upward, the tube 14 has upward momentum as the fluid travels therethrough, the fluid entering the tube 14 through the proximal portion 14A resists the vertical upward motion of the tube 14 by pushing downward on the leg of the tube 14 nearest the fluid inlet 22, and the fluid exiting the tube 14 through the proximal portion 14B resists having its upward vertical motion (acquired from the tube 14) decreased by pushing upward on the leg of the tube 14 nearest the fluid outlet 24. The resulting forces cause the tube 14 to twist about its axis of symmetry 36. In FIGS. 1 through 4, the axis of symmetry 36 extends from the base 16 to the distal portion 14C of the tube 14, whereas in FIG. 6 the axis of symmetry 36 is along the axis of the tube 14 between the portions 16A and 16B of the base 16. As the tube 14 moves downward during the second half of its vibration cycle, the tube 14 twists in the opposite direction. This twisting characteristic is referred to as the Coriolis effect, and the degree to which the tube 14 deflects during a vibration cycle as a result of the Coriolis effect can be correlated to the mass flow rate of the fluid flowing through the tube 14, while the density of the fluid is proportional to the frequency of vibration at resonance.

Though necessary to the operation and sensing technique used by the MEMS devices 10, the twisting motion of the tube 14 applies mechanical stresses to the attachment between the tube 14 and base 16, resulting in clamping losses that must be dissipated to the substrate 12 and any additional packaging in which the device 10 is enclosed. A desired aspect of the invention is intended to reduce these losses by the inclusion of additional mass attached to the tube 14 by a flexible attachment to enable the mass to vibrate out of phase with the tube 14. In the Figures, such a mass is represented by a cantilevered member 30 that projects roughly perpendicularly from the distal portion 14C of the tube 14, and more particularly at the axis of symmetry 36 of the tube 14 about which the tube 14 twists due to the Coriolis effect. The member 30 is shown in FIGS. 1 through 4 as disposed within an opening defined and surrounded by the tube 14 and base 16, though it is also within the scope of the invention that the member 30 could project outward the tube 14. The member 30 defines a pivot axis 32 about which the member 30 pivots relative to the distal portion 14C of the tube 14. The member 30 is effectively a counterbalance to the combined mass of the tube 14 and any fluid flowing through the tube 14. By configuring and attaching the member 30 to that its vibration is opposite the tube 14, in other words, the member 30 vibrates approximately 180 degrees out of phase with the tube 14, the vibrational movement of the member 30 sufficiently counteracts the vibrational movement of the tube 14 to reduce mechanical (clamping) losses dissipated to the substrate 12.

Figure 7:
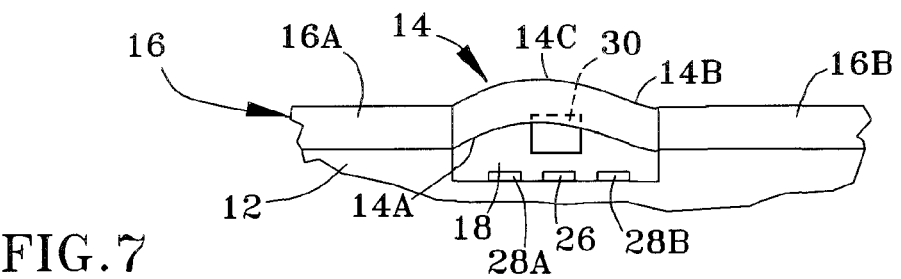
FIG. 7 is a side view showing the tube and cantilevered member of the device of FIG. 6 vibrating out of phase with each other.

In each of FIGS. 1 through 4 and 6, the cantilevered member 30 is configured to have a rectangular shape when viewed from above, though other shapes are also within the scope of the invention. The Figures also show the member 30 as being attached to the tube 14 via a pivot arm 34 having a reduced cross-section relative to the member 30 so as to concentrate flexure of the member 30 adjacent the tube 14. However, it is foreseeable that the member 30 could be directly attached to the tube 14 if the attachment point and/or the member 30 are constructed to be adequately flexible. As evident from FIG. 5, which depict the half of the vibration cycle in which the tubes 14 of FIGS. 1 through 4 travel upward, as the distal portion 14C of the tube 14 pivots upward relative to the base 16, the member 30 pivots downward relative to the distal portion 14C. The opposite motions occur during the second half of the vibration cycle of the tube 14. In FIG. 7, which depicts the half of the vibration cycle in which the tube 14 travels upward, the distal portion 14C of the tube 14 is deflected upward relative to the proximal portions 14A and 14B. The opposite motions occur during the second half of the vibration cycle of the tube 14.

Each of the above out-of-phase vibrational modes has the ability to reduce the mechanical losses that must be dissipated to the substrate 12. The ability to minimize mechanical losses improves as the masses of the tube 14 and member 30 become closer, with optimal results believed to occur when the masses of the tube 14 and member 30 are approximately equal. Consequently, the size and shape of the member 30 will depend in part on the tube configuration, as well as the density of particular fluid flowing through the device 10. The resonant frequencies of the tube 14 and member 30 are influenced by their mechanical design (shape, size, mass, construction and materials), which can be optimized for a particular application using, for example, known finite element modeling. For many applications, suitable resonant frequencies will generally be in a range of about 1 kHz to about 150 kHz.

The relative amplitudes of vibration for the tube 14 and member 30 will also be determined by their respective mechanical designs, while amplitude as a whole can be adjusted through the means used to vibrate the tube 14 and member 30. For this purpose, FIGS. 1 through 4 and 6 show a drive electrode 26 located on the surface 18 of the substrate 12 beneath either the cantilevered member 30 or the distal portion 14C of the tube 14. In FIGS. 1, 3, 4 and 6, the drive electrode 26 is located directly beneath the member 30, while in FIG. 2 the drive electrode 26 is located directly beneath the distal portion 14C of the tube 14. In the former case, direct inducement of vibration in the member 30 serves to indirectly induce vibration in the tube 14, and in the latter case direct inducement of vibration in the tube 14 indirectly induces vibration in the member 30. It is also within the scope of this invention to place drive electrodes 26 beneath the cantilevered member 30 and the distal portion 14C of the tube 14.

If formed of an electrically-conductive material, such as doped silicon, the tube 14 can serve as an electrode that can be capacitively coupled to the drive electrode 26, enabling the electrode 26 to electrostatically drive the tube 14. However, it is foreseeable that the tube 14 could be formed of a nonconductive material, and a separate electrode formed on the tube 14 facing the electrode 26 for vibrating the tube 14 electrostatically. An alternative driving technique shown in FIG. 3 is to provide a film 40 on the upper surface of the tube 14 for vibrating the tube 14 electromagnetically or piezoelectrically (for convenience, FIG. 3 represents a plan view of only the micromachine level of the device 10, and omits the substrate 12 and metallized level of the device 10). For example, forming the film 40 of a magnetic material enables the tube 14 to be driven electromagnetically with an electromagnet positioned above the tube 14 (not shown). Alternatively, the film 40 can be formed as a piezoelectric element to generate alternating forces in the plane of the tube 14 that flex the tube 14 in directions normal to the plane of the tube 14. Other alternative driving techniques include thermal, piezoresistive, optical, and other actuation technique.

The Figures further show sensing electrodes 28 arranged in at least two pairs 28A-D to sense the deflection of the tube 14 relative to the substrate 12, as well as provide feedback to the drive electrode 26 to enable the vibration frequency to be controlled with any suitable on-chip or remote microprocessor or microcontroller 42. The sensing electrodes 28 can sense the proximity or motion of the tube 14 capacitively, electrostatically, electromagnetically, piezoelectrically, piezoresistively, thermally, optically, or in any other suitable manner capable of sensing the proximity or motion of the tube 14. Furthermore, the degree to which the tube 14 twists during a vibration cycle as a result of the Coriolis effect can be detected by the sensing electrodes 28 on the basis of the amplitude of the deflection and/or the phase difference between the respective sides (legs) of the tube 14 nearest each electrode 28A, 28B, 28C and 28D. Input and output signals to the electrodes 26 and 28 (and the magnetic/piezoelectric film 40 of FIG. 3) can be made through bond pads 44 along an edge of the substrate 12, and are transmitted to the microcontroller 42 with appropriate signal conditioning circuitry 46, as schematically represented in FIGS. 1 through 4 and 6. Ground contacts 48 are shown as being formed in the same metal layer as that used to form the electrodes 26 and 28 and bond pads 44, and by which an electrical ground to the tube base 16 is provided to enable the tube 14 or an electrode formed on the tube 14 to be capacitively coupled to the drive electrode 26.

Though represented as solid in FIGS. 1 through 3 and 5 through 7, the member 30 can be hollow to contain a sealed gas or vacuum chamber. The inclusion of a hollow chamber enables the use of a larger member 30 to increase the electrostatic force that can be applied by the drive electrode 26 to vibrate the tube 14 into resonance. Alternatively, FIG. 4 represents an embodiment in which the member 30 is fabricated to have an internal chamber 38 into which fluid within the tube 14 can enter the member 30, with the result that the mass of the member 30 is influenced by the fluid being evaluated. (Similar to FIG. 3, FIG. 4 represents a plan view of only the micromachine level of the device 10 and omits the substrate 12 and metallized level of the device 10.) In this manner, the vibrational mass of the member 30 is less when evaluating a relatively low-density fluid, including gases, and is greater when evaluating a relatively denser fluid. Various fluid paths through the member 30 are also possible, including flow paths with no stagnant sections.

The accuracy of measurements made with the devices 10 can be improved by monitoring the temperature of the fluid. For this purpose, the devices 10 are represented as equipped with a temperature sensing element 50. A suitable construction for the sensing element 50 can make use of one or more metal layers of the type employed to form the electrodes 26 and 28 and their associated conductive runners. For example, a resistive-based temperature sensing element 50 can be formed by a thin-film metal layer of gold, platinum, palladium, chromium, nickel, or another metal or alloy, in accordance with known practices. With the temperature sensing element 50, changes in mechanical properties of the tube 14 and properties of the fluid therein attributable to temperature changes can be compensated for with the signal conditioning circuitry 46.

The MEMS devices 10 of FIGS. 1 through 7 can be enclosed by a capping wafer (not shown) to form a sensing package. The use of a capping wafer allows for vacuum packaging that reduces air damping of the tube vibration. A variety of package and wafer-level methods exist to vacuum package devices. These include solder or weld hermetic packages, and wafer bonding using glass frit, solder, eutectic alloy, adhesive, and anodic bonding. Silicon is a particular example of a suitable material for the capping wafer, which has the advantage of allowing silicon-to-silicon bonding techniques to be used, though it is foreseeable that a variety of other materials could be used, including metals and glass materials, the latter including borosilicate glass (e.g., Pyrex). Notably, the reduced mechanical losses made possible with this invention may enable the devices 10 to be packaged in less expensive plastic packages and/or over molded. Reduced mechanical losses also offer the possibility of the sensor package being able to withstand greater mechanical stress without adversely impacting the performance of the device 10.

In preferred embodiments of the invention, the bond between the capping wafer and substrate 12 is hermetic, and the resulting enclosure is evacuated to enable the tube 14 to be driven efficiently at high quality (Q) factor values without damping. In such an embodiment, a getter material is preferably placed in the enclosure to assist in reducing and maintaining a low cavity pressure. As an alternative to a hermetically sealed package, the tube 14 could be enclosed such that a vacuum can be drawn when desired through the use of a pump.

If a magnetic or piezoelectric actuation scheme is employed to drive the tube 14 as represented in FIG. 3, the device 10 can operate with larger gaps between the tube 14 and substrate 12, with the potential for sufficiently reducing squeeze film damping of the tube 14 to eliminate the need for vacuum packaging of the device 10.

While the invention has been described in terms of certain embodiments, it is apparent that other forms could be adopted by one skilled in the art. Therefore, the scope of the invention is to be limited only by the following claims.

The invention claimed is:

1. A MEMS device for determining at least one property of a fluid, the device comprising:

a substrate;

a structure on the substrate, the structure comprising a base attached to the substrate and a tube attached to and extending from the base and spaced apart from a surface of the substrate so as to be capable of vibrational movement relative to the base and the substrate in a plane normal to the surface of the substrate, the tube comprising a continuous internal passage, a fluid inlet and a fluid outlet of the internal passage fluidically connected to the base, and a distal portion relative to the base, the vibrational movement of the tube comprising a twisting motion that applies mechanical stresses to an attachment between the tube and base resulting in clamping losses that are dissipated through the base to the substrate;

a cantilevered member attached to the distal portion of the tube and configured for vibrational movement relative to the distal portion and in a plane normal to the surface of the substrate, wherein the vibrational movement of the cantilevered member counteracts the vibrational movement of the tube to minimize clamping losses dissipated to the substrate;

at least one drive electrode on the surface of the substrate, adjacent at least one of the cantilevered member and the distal portion of the tube, and operable to induce the vibrational movements of the tube and the cantilevered member;

sensing electrodes on the surface of the substrate, the sensing electrodes being adapted to sense deflections of the tube when vibrated with the drive electrode and produce outputs corresponding to the sensed deflections; and means for determining from the outputs of the sensing electrodes at least one property of a fluid flowing through the internal passage.

2. The MEMS device according to claim 1, wherein the cantilevered member comprises a reduced section between the cantilevered member and the distal portion of the tube, and the tube, the cantilevered member, and the reduced section are configured so that flexure during the vibrational movement of the cantilevered member is concentrated in the reduced section.

3. The MEMS device according to claim 1, wherein the tube and the cantilevered member are configured so that the vibrational movement of the cantilevered member is about 180 degrees out of phase with the vibrational movement of the tube.

4. The MEMS device according to claim 1, wherein the cantilevered member and the tube have approximately equal masses.

5. The MEMS device according to claim 1, wherein the at least one drive electrode is disposed beneath the cantilevered member on the surface of the substrate, and is adapted to directly induce the vibrational movement of the cantilevered member and indirectly induce the vibrational movement of the tube.

6. The MEMS device according to claim 1, wherein the at least one drive electrode is disposed beneath the distal portion of the tube on the surface of the substrate, and is adapted to directly induce the vibrational movement of the tube and indirectly induce the vibrational movement of the cantilevered member.

7. The MEMS device according to claim 1, wherein the at least one drive electrode is operable to induce the vibrational movements of the tube and the cantilevered member either electrostatically, electromagnetically, piezoresistively, piezoelectrically, thermally, or optically.

8. The MEMS device according to claim 1, further comprising a film on the cantilevered member or the distal portion of the tube for electromagnetically or piezoelectrically coupling with the at least one drive electrode to electromagnetically or piezoelectrically induce the vibrational movements of the tube and the cantilevered member.

9. The MEMS device according to claim 8, wherein a sufficiently large gap exists between the tube and the substrate to reduce squeeze film damping of the tube, and the tube is not enclosed in a vacuum package.

10. The MEMS device according to claim 1, wherein the tube has a shape chosen from the group consisting of U-shaped, C-shaped, and linear.

11. The MEMS device according to claim 1, wherein the tube has a U-shape or C-shape, oppositely-disposed ends of the tube are attached to the base, and the distal portion of the tube is midway between the ends of the tube, and the cantilevered member extends perpendicularly from the distal portion of the tube.

12. The MEMS device according to claim 11, wherein the base and the tube define and surround an opening in which the cantilevered member is disposed.

13. The MEMS device according to claim 1, wherein the tube has a linear shape, oppositely-disposed ends of the tube are attached to spaced-apart portions of the base, the distal portion of the tube is midway between the ends of the tube, and the cantilevered member extends perpendicularly from the distal portion of the tube.

14. The MEMS device according to claim 1, wherein the cantilevered member comprises an internal chamber.

15. The MEMS device according to claim 14, wherein the internal chamber is fluidically coupled to the internal passage of the tube.

16. The MEMS device according to claim 1, wherein the MEMS device is installed in a system chosen from the group consisting of chemical concentration sensors, fuel deliver/handling systems, fuel cell systems, and drug delivery systems.

17. A method of operating the MEMS device of claim 1 to sense the at least one property of the fluid, the method comprising:

operating the at least one drive electrode to induce the vibrational movements of the tube and the cantilevered member as the fluid flows through the internal passage within the tube so that the vibrational motion of the cantilevered member is not in phase with the vibrational motion of the tube and counteracts the vibrational movement of the tube to minimize clamping losses dissipated to the substrate;

operating the sensing electrodes to sense deflections of the tube relative to the substrate;

producing outputs corresponding to the sensed deflections; and determining from the outputs the at least one property of the fluid.

18. The method according to claim 17, wherein the vibrational movement of the cantilevered member is about 180 degrees out of phase with the vibrational movement of the tube.

19. The method according to claim 17, wherein the at least one drive electrode is disposed beneath the cantilevered member on the surface of the substrate, directly induces the vibrational movement of the cantilevered member, and indirectly induces the vibrational movement of the tube.

20. The method according to claim 17, wherein the at least one drive electrode is disposed beneath the distal portion of the tube on the surface of the substrate, directly induces the vibrational movement of the tube, and indirectly induces the vibrational movement of the cantilevered member.

21. The method according to claim 17, wherein the at least one drive electrode induces the vibrational movements of the tube and the cantilevered member either electrostatically, electromagnetically, piezoresistively, piezoelectrically, thermally, or optically.

22. The method according to claim 17, wherein the at least one drive electrode is electromagnetically coupled with a magnetic film on the cantilevered member or the distal portion of the tube to electromagnetically induce the vibrational movements of the tube and the cantilevered member.

23. The method according to claim 17, wherein the cantilevered member comprises an internal chamber fluidically coupled to the internal passage of the tube, and at least a portion of the fluid flows into and then out of the internal chamber as the fluid flows through the internal passage of the tube.

24. The method according to claim 17, wherein the at least one property of the fluid is chosen from the group consisting of mass flow rate, density, specific gravity, volumetric flow rate, chemical concentration, viscosity, and lubricity, of the fluid.

* * * * *